United States Patent [19]

Liebenow et al.

[11] 4,125,721
[45] Nov. 14, 1978

[54] PROCESS FOR THE PRODUCTION OF 2,4-DIAMINO-5-(3',4',5'-TRIMETHOXYBEN-ZYL)-PYRIMIDINE

[75] Inventors: Walter Liebenow, Nuremberg; Jaroslav Prikryl, Erlangen-Bruck, both of Germany

[73] Assignee: Ludwig Heumann & Co. GmbH, Nuremberg, Germany

[21] Appl. No.: 820,413

[22] Filed: Aug. 1, 1977

[30] Foreign Application Priority Data

Aug. 9, 1976 [DE] Fed. Rep. of Germany ....... 2635765

[51] Int. Cl.² .................................... C07D 239/48
[52] U.S. Cl. ............................ 544/325; 260/465 F
[58] Field of Search ............................... 260/256.4 N

[56] References Cited
U.S. PATENT DOCUMENTS

| | | | |
|---|---|---|---|
| 2,909,522 | 10/1959 | Hitchings et al. | 260/256.4 N |
| 3,341,541 | 9/1967 | Hoffer | 260/256.4 N |
| 3,849,470 | 11/1974 | Cresswell et al. | 260/256.4 N |

Primary Examiner—Paul M. Coughlan, Jr.

[57] ABSTRACT

A process for the production of 2,4-diamino-5-(3',4',5'-trimethoxybenzyl)-pyrimidine by condensing trimethoxy benzaldehyde with a substituted propionitrile compound and reacting the condensation product obtained with guanidine, wherein a β-akyl-(aryl-, benzyl-)-oxy-ethyleneoxy-propionitrile corresponding to the formula

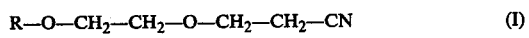

$$R-O-CH_2-CH_2-O-CH_2-CH_2-CN \quad (I)$$

in which R represents an alkyl group, an optionally substituted phenyl group or a benzyl group, is condensed with trimethoxy benzaldehyde in the presence of basic reagents to form a compound corresponding to the general formula

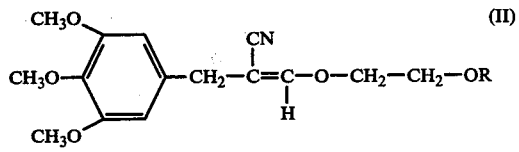

(II)

in which R is as defined above, and the condensation product (II) obtained is reacted with guanidine in known manner to form 2,4-diamino-5-(3',4',5'-trimethoxybenzyl)-pyrimidine.

3 Claims, No Drawings

PROCESS FOR THE PRODUCTION OF 2,4-DIAMINO-5-(3',4',5'-TRIMETHOXYBENZYL)-PYRIMIDINE

This invention relates to a new process for the production of 2,4-diamino-5-(3',4',5'-trimethoxybenzyl)-pyrimidine.

The compound 2,4-diamino-5-(3',4',5'-trimethoxybenzyl)-pyrimidine (trimethoprim) is highly active against various germs, such as for example proteus vulgaris, and in combination with a sulphonamide represents a valuable medicament.

There are already various processes for producing benzyl pyrimidine compounds of the trimethoprim type.

Thus, in the process according to German Pat. No. 1,445,176, a correspondingly substituted benzaldehyde is condensed with a propionitrile substituted in the β-position by an alkoxy, alkylmercapto or dialkylamino group in the usual way under strongly basic reaction conditions and the nitrile mixture obtained, which corresponds to the general formulae (A) and (B)

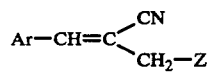 (A)

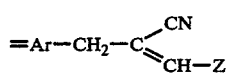 (B)

is reacted in the usual way with guanidine. However, the nitrile mixture obtained by this known process contains the benzal compound of general formula (A) in a proportion of 80%, whilst the corresponding benzyl compound (B) is only present in a proportion of approximately 20%. Since, in the subsequent reaction with guanidine, it is only the benzyl compound which closes the ring to form the required benzyl pyrimidine, the 2,4-diamino-5-(3',4',5'-trimethoxybenzyl)-pyrimidine can only be obtained in a yield of approximately 28% by this known process which is unsatisfactory.

Accordingly, in another known process according to German Offenlegungsschrift No. 1,620,729, the yield is improved by condensing the correspondingly substituted benzaldehyde with a β-substituted propionitrile corresponding to the formula

ROCH$_2$CH$_2$CN in which R represents an alkyl group with 1 to 4 carbon atoms, to form a compound corresponding to the general formula

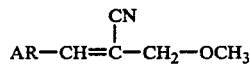

and converting this compound by heating for 24 hours in methanol in the presence of methylate ions into the acetal

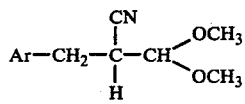

which is then reacted with guanidine by heating for another 20 hours in ethanol to form the required benzyl pyrimidine. This known process is also unsatisfactory on account of its only moderate yield and the very long reaction times.

In both known processes, little practical significance is attributed to the substituents Z or R of the propionitrile because this substituent is eliminated with the guanidine during the reaction.

The object of the present invention is to provide a process for the production of 2,4-diamino-5-(3',4',5'-trimethoxybenzyl)-pyrimidine by which high yields of this compound are quickly obtained in a simple reaction.

This object is achieved by the invention.

Accordingly, the present invention relates to a process for the production of 2,4-diamino-5-(3',4',5'-trimethoxybenzyl)-pyrimidine by condensing trimethoxy benzaldehyde with a substituted propionitrile compound and reacting the condensation product obtained with guanidine, wherein a β-alkyl-(aryl-benzyl-)-oxyethyleneoxy-propionitrile corresponding to the formula

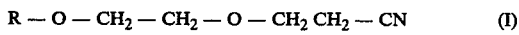 (I)

in which R represents an alkyl group, an optionally substituted phenyl group or a benzyl group,
is condensed with trimethoxy benzaldehyde in the presence of basic reagents to form a compound corresponding to the general formula

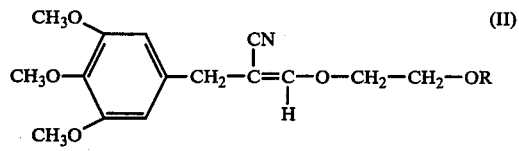 (II)

in which R is as defined, above, and the condensation product (II) obtained is reacted with guanidine in known manner to form 2,4-diamino-5-(3',4',5'-trimethoxybenzyl)-pyrimidine.

In the process according to the invention, it is preferred to use a β-substituted propionitrile of general formula (I) in which R represents a straight-chain lower alkyl group, for example a methyl or ethyl group or a phenyl or benzyl group, although the reaction is also successful where R represents a long-chain or branched-chain alkyl group or a substituted phenyl group, the phenyl group optionally being substituted for example by a halogen atom, a nitro group, a lower alkyl group and/or an alkoxy group.

The first stage of the process according to the invention, in which the β-substituted propionitrile is condensed with trimethoxy benzaldehyde, is preferably carried out in a solvent. Suitable solvents are, for example, alkoxy alkanols such as the monomethyl, monoethyl and monophenyl ethers of ethylene glycol and the like.

The reaction temperature is in the range from 50° to 120° C. and preferably in the range from 90° to 100° C. This reaction may be carried out under pressures in the range from 0 to 5 bars, although the reaction is preferably carried out at atmospheric pressure. The molar ratio of substituted propionitrile to trimethoxy benzaldehyde amounts to between 1 : 1 and 1 : 2 and preferably to 1 : 1.3.

The following compounds may be used as basic reagents: alkoxides, anhydrous bases, for example sodium methoxide sodium ethoxide, potassium tert.-butoxide, sodium hydroxide, potassium hydroxide, and also organic bases such as, for example, benzyl trimethyl ammonium hydroxide.

In one preferred embodiment of the invention, the basic reagent is prepared by reacting sodium with the ethylene glycolether, for example the monomethyl ether of ethylene glycol (methylglycol) used as solvent. The basic reagent is used in a proportion of from 1 to 10% by weight and preferably in a proportion of from 3 to 6% by weight.

On completion of the reaction, the residual solvent is distilled off and the condensation product is isolated in known manner, for example by taking up the residue left after the solvent has been distilled off in a solvent, such as dichloroethane for example, washing the organic phase with water until it shows a neutral reaction, drying it with a drying agent, such as calcium chloride for example, evaporating off the solvent and distilling the residue obtained.

In the second stage, the condensation product thus obtained is reacted in the usual way with guanidine to form the required 2,4-diamino-5-(3',4',5'-trimethoxybenzyl)-pyrimidine. This reaction is also carried out in a solvent such as, for example, methyl glycol or in any of the solvents mentioned above.

The reaction temperature is in the range from 65° to 145° C. and preferably in the range from 100° to 120° C. This reaction may be carried out at pressures in the range from 0 bar to 5 bars, although it is preferably carried out at atmospheric pressure. The molar ratio of II to guanidine amounts to between 1 : 1 and 1 : 5 and preferably to between 1 : 2 and 1 : 3.

The guanidine used in this stage is best produced beforehand from guanidine hydrochloride by reaction with a base, for example a sodium methoxide solution.

On completion of the reaction, the solvent is distilled off and the required product is precipitated from the cooled reaction mixture by adding water and optionally purified by recrystallisation.

By virtue of the fact that the benzyl compound (II) is formed in a proportion of 80% in the first stage of the process according to the invention, it is possible to obtain the required 2,4-diamino-5-(3',4',5'-trimethoxybenzyl)-pyrimidine in a yield of more than 80% over a reaction time of only 1 to 2 hours. By contrast, the yield of 2,4-diamino-5-(3',4',5'-trimethoxybenzyl)-pyrimidine obtained in the process according to German Pat. No. 1,445,176 amounts to only 40% where β-ethoxypropionitrile is used as the starting compound.

The invention is illustrated by the following Examples.

EXAMPLE 1

Production of α-(3,4,5-trimethoxybenzyl)-β-(2-methoxyethoxy)-acrylonitrile:

5 liters of methyl glycol are introduced into a 10 liter flask, followed by the introduction under nitrogen with stirring of 46 g of sodium in the form of small lumps. Once all the sodium has dissolved, 878 g (6.8 moles) of β-(methoxyethoxy)-propionitrile are run in at a temperature of 50° C. The internal temperature rises to 95° C. At this temperature 1170 g (6.0 moles) of trimethoxy benzaldehyde are added in portions and 1.6 liters of solvent are distilled off over a period of about 45 minutes at a temperature of 127° C. The rest of the solvent is distilled off in a water jet vacuum. The residue is then taken up in 4 liters of dichloroethane, the organic phase is washed with water until neutral, subsequently dried with calcium chloride and the dichloroethane evaporated off in a water jet vacuum.

The brownish oily residue gives a yield of 1545 g.

The product distills in the form of a mixture of cis-trans isomers in the boiling range from 165° to 185° C./0.1 Torr.

EXAMPLE 2

Production of 2,4-diamino-5-(3',4',5'-trimethoxybenzyl)-pyrimidine:

A guanidine solution is initially prepared by dissolving 476 g (5.0 moles) of guanidine hydrochloride in 800 ml of methanol, adding 920 ml of a 5.5-molar sodium methoxide solution and filtering the sodium chloride precipitated.

This solution is added dropwise at 95° C. to a solution of 460 g (1.5 moles) of α-(3,4,5-trimethoxybenzyl)-β-(2-methoxyethoxy)-acrylonitrile in 1 liter of methyl glycol, the methanol simultaneously distilling off from the reaction solution. After the guanidine solution has been added and the methanol removed, the temperature is increased to 120° C. and the reaction solution is left standing for 1 hour at that temperature. The solvent is distilled off until a solid residue remains. 3.5. liters of water are added to the cool reaction mixture and the required product is filtered off under suction.

Yield: 360 g. Melting point: 199° to 200° C.

EXAMPLE 3

Production of α-(3',4',5'-trimethoxybenzal)-β-(2-methoxyethoxy)-propionitrile:

46 g of sodium in the form of small lumps are introduced under nitrogen with stirring into 5 liters of methyl glycol in a 10-liter capacity flask. After all the sodium has dissolved, 878 g (6.8 moles) of β-(methoxyethoxy)-propionitrile are run in at 50° C., followed after 5 minutes by the addition in portions of 1170 g (6.0 moles) of trimethoxybenzaldehyde, after which the solution is stirred at an internal temperature of 50° C. Methyl glycol is then distilled off in vacuo, the residue is taken up in 4 liters of dichloroethane, the organic phase is washed with water until neutral and then dried with calcium chloride. The dichloroethane is then distilled off in a water jet vacuum and the oily residue is distilled in vacuo.

Yield 1075 g = 87% of the theoretical, based on trimethoxybenzaldehyde. B.p.: 165°–185° C./0.01 bar.

EXAMPLE 4

Production of 2,4-diamino-5-(3',4',5'-trimethoxybenzyl)-pyrimidine:

In a 3-liter flask, 55 g of sodium are dissolved in 500 ml of methyl glycol. 307 g (1 mole) of α-(3',4',5'-trimethoxybenzal)-β-(2-methoxyethoxy)-propionitrile in 200 ml of methyl glycol are run in at 90° to 95° C. and the entire solution is kept at that temperature for 5 to 10 mins. 260 g (2.75 mole) of guanidine hydrochloride are added to the "benzyl compound" formed without isolation, followed by heating with stirring for 4 hours to 120° C. Methyl glycol is then distilled off to leave a solid residue which is stirred with 800 ml of water, after which the required crude product is filtered under suction and washed once more with water. Yield: 246 g = 86% of the theoretical.

We claim:

1. A process for the production of 2,4-diamino-5-(3',4',5'-trimethoxybenzyl)-pyrimidine by condensing trimethoxy benzaldehyde with a substituted propionitrile compound and reacting the condensation product obtained with guanidine, wherein a β-[alkyl-(aryl-, benzyl-)-oxy-ethyleneoxy-] substituted propionitrile corresponding to the formula

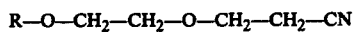

in which R is selected from the group consisting of alkyl, phenyl, phenyl subsituted by a halogen atom, a nitro group, a lower alkyl group or an alkoxy group and benzyl, is condensed with trimethoxy benzaldehyde in the presence of basic reagents to form a compound corresponding to the general formula

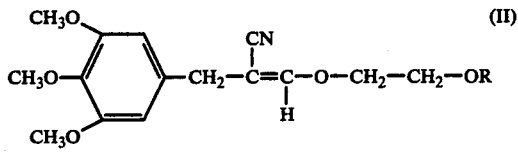

in which R is as defined above, and the condensation product (II) obtained is reacted with guanidine [in known manner] to form 2,4-diamino-5-(3',4',5'-trimethoxybenzyl)-pyrimidine.

2. A process as claimed in claim 1, wherein a β-substituted propionitrile of general formula (I), in which R is a straight-chain lower alkyl group, is used.

3. A process as claimed in claim 1, wherein the reaction of the β-substituted propionitrile with trimethoxy benzaldehyde and the reaction of the condensation product (II) with guanidine are carried out in a solvent.

* * * * *